United States Patent
Marchionni et al.

(10) Patent No.: US 6,858,757 B2
(45) Date of Patent: *Feb. 22, 2005

(54) PROCESS FOR PREPARING PERFLUOROPOLYOXYALKYLENES WITH -OCF$_2$H, -OCF$_2$CF$_2$H AND -OCF(CF$_3$)H END GROUPS

(75) Inventors: Giuseppe Marchionni, Milan (IT); Gianfranco Spataro, Milan (IT)

(73) Assignee: Solvay Solexsis S.p.A., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 10/442,145

(22) Filed: May 21, 2003

(65) Prior Publication Data

US 2003/0220527 A1 Nov. 27, 2003

(30) Foreign Application Priority Data

May 21, 2002 (IT) .................................... MI2002A1081

(51) Int. Cl.$^7$ ............................................... C07O 43/11
(52) U.S. Cl. .................................... 568/615; 568/617
(58) Field of Search ................................ 568/560, 561, 568/565

(56) References Cited

U.S. PATENT DOCUMENTS 5,969,192 A * 10/1999 Marchionni et al. ........ 568/615

FOREIGN PATENT DOCUMENTS

EP      0 695 775 A1     7/1996

* cited by examiner

Primary Examiner—Karl Puttlitz
(74) Attorney, Agent, or Firm—Arent Fox PLLC

(57) ABSTRACT

A process for preparing perfluoropolyoxyalkylenes having —OCF$_2$H, —OCF$_2$CF$_2$H and —OCF(CF$_3$)H end groups and a number average molecular weight from 120 to 3,000, by decarboxylation of the corresponding perfluoropolyoxyalkylenes having —OCF$_2$COOH, —OCF$_2$CF$_2$COOH, —OCF(CF$_3$)COOH end groups, in the presence of catalytic amounts of salts formed by perfluoropolyoxyalkylenes having end groups selected from —OCF$_2$COOZ, —OCF$_2$CF$_2$COOZ and —OCF(CF$_3$)COOZ, wherein Z is a monovalent cation of the group Ia or Ib or Z is —NR$_4^+$ wherein R is hydrogen or a C$_1$–C$_4$ alkyl, using ratios between Z and the —COOH equivalents of the perfluoropolyoxyalkylenes to be decarboxylated from 0.01 to 0.08, at a temperature between 120° C. and 180° C., in the presence of water, at pH <5 and at a pressure comprised between 2 and 80 atmospheres.

8 Claims, No Drawings

PROCESS FOR PREPARING PERFLUOROPOLYOXYALKYLENES WITH -OCF₂H, -OCF₂CF₂H AND -OCF(CF₃)H END GROUPS

The present invention relates to a process for preparing perfluoropolyoxyalkylenes having at least one hydrogenated end group selected from —OCF$_2$H, —OCF$_2$CF$_2$H and —OCF(CF$_3$)H and a number average molecular weight from 120 to 3,000 by decarboxylation of perfluoropolyoxyalkylenes having at least one end group —OCF$_2$COOH, —OCF$_2$CF$_2$COOH, —OCF(CF$_3$)COOH in the presence of catalytic amounts of carboxylic acid salts of perfluoropolyoxyalkylenes.

The perfluoropolyoxyalkylenes having the above hydrogenated end groups and number average molecular weight from 120 to 3,000 can be used as refrigerants, heat exchange agents, foaming agents, propellants for aerosol, working fluids and as solvents in substitution of CFCs and HCFCs which have been banned owing to their harmful environmental impact. In fact said perfluoropolyoxyalkylenes are not toxic, have an impact on the ozone equal to zero (ODP=0) and a low potential greenhouse effect (GWP).

It is known from EP 695,775 to prepare perfluoropolyoxyalkylenes having hydrogenated end groups of the above type by a decarboxylation of the alkaline salts of the corresponding perfluoropolyoxyalkylenes with —OCF$_2$COOH, —OCF$_2$CF$_2$COOH and —OCF(CF$_3$)COOH end groups in aqueous medium at pH between 5 and 9 at temperatures in the range 140° C.–170° C. and at a pressure of at least 4 atm.

Said process is disadvantageous for the high amount of bases used in the salification and for the formation in the reaction of high amounts of carbonates and/or bicarbonates difficult to handle and to separate. Therefore said process carried out in an industrial plant requires purgers to remove carbonates and/or bicarbonates. In said operation also significant amounts of perfluoropolyoxyalkylene salts to be decarboxylated are lost. By considering the high cost of the salts to be decarboxylated, it is necessary to use additional plant units.

It has been unexpectedly and surprisingly found that it is possible to avoid the drawbacks of the known process using the invention process described hereinafter.

An object of the present invention is a process for preparing perfluoropolyoxyalkylenes having one or two end groups selected from —OCF$_2$H, —OCF$_2$CF$_2$H and —OCF(CF$_3$)H and a number average molecular weight from 120 to 3,000, comprising the decarboxylation of the corresponding perfluoropolyoxyalkylenes having one or two end groups selected from —OCF$_2$COOH, —OCF$_2$CF$_2$COOH and —OCF(CF$_3$)COOH in the presence of catalytic amounts of salts of perfluoropolyoxyalkylenes having one or two end groups selected from —OCF$_2$COOZ, —OCF$_2$CF$_2$COOZ and —OCF(CF$_3$)COOZ, wherein Z is a monovalent cation selected from the groups Ia and Ib of the Periodic System of the Elements, having ionic radius $\geq$0.95 Å or Z is —NR$_4^+$ wherein R is hydrogen or a C$_1$–C$_4$ alkyl, using ratios between Z and the —COOH equivalents of the perfluoropolyoxyalkylenes to be decarboxylated from 0.01 to 0.08, preferably from 0.01 to 0.05, at a temperature between 120° C. and 180° C., in the presence of water, at pH<5 and at a pressure comprised between 2 and 80 atmospheres, preferably between 3 and 40 atmospheres.

The perfluoropolyoxyalkylenes having at least one end group —OCF$_2$COOH, —OCF$_2$CF$_2$COOH and —OCF(CF$_3$)COOH are formed by perfluorooxyalkylene repeating units, said units being statistically distributed along the polymeric chain, selected from (CF$_2$CF$_2$O), (CF$_2$O), (CF$_2$CF(CF$_3$)O), (CF(CF$_3$)CF$_2$O), (CF(CF$_3$)O), (CF$_2$CF$_2$CF$_2$O), (CF$_2$CF(OX)O), (CF(OX)O), wherein X is —(R'O)$_u$R" with R'=—CF$_2$—, —CF$_2$CF$_2$—, —CF$_2$CF(CF$_3$)— and u is an integer from 0 to 6 and where R" is —(CF$_2$)$_k$CF$_3$ and k is an integer from 0 to 4.

More specifically the perfluoropolyoxyalkylenes having at least one end group —OCF$_2$COOH, —OCF$_2$CF$_2$COOH and —OCF(CF$_3$)COOH have the following structures:

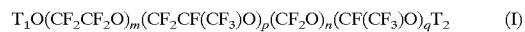  (I)

  (II)

  (III)

  (IV)

  (V)

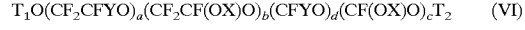  (VI)

wherein T$_2$ is selected from —CF$_2$COOH, —CF$_2$CF$_2$COOH, —CF(CF$_3$)COOH; T$_1$ is selected from —CF$_3$, —C$_2$F$_5$, —C$_3$F$_7$, —CF$_2$COOH, —CF$_2$CF$_2$COOH, —CF(CF$_3$)COOH; Y=—F, —CF$_3$, and X is —(R'O)$_u$R" with R'=—CF$_2$—, —CF$_2$CF$_2$—, —CF$_2$CF(CF$_3$)— and u is an integer from 0 to 6 and where R" is —(CF$_2$)$_k$CF$_3$ and k is an integer from 0 to 4; r is 0 or 1 and a, b, c, d, m, n, p, q, and s have average values such that the number average molecular weight is comprised between 120 and 3,000.

The perfluoropolyoxyalkylenes having at least one carboxylic end group —OCF$_2$COOH, —OCF$_2$CF$_2$COOH, —OCF(CF$_3$)COOH are prepared through hydrolysis of the corresponding perfluoropolyoxyalkylenes having one or two acylfluoride end groups selected from —OCF$_2$COF, —OCF$_2$CF$_2$COF and —OCF(CF$_3$)COF, subsequent HF separation by distillation or separation of the aqueous HF phase if water in excess is used.

The perfluoropolyoxyalkylenes with at least one acylfluoride end group are compounds known as such and are formed by perfluorooxyalkylene repeating units, said units being statistically distributed along the polymeric chain, selected from (CF$_2$CF$_2$O), (CF$_2$O), (CF$_2$CF(CF$_3$)O), (CF(CF$_3$)CF$_2$O), (CF(CF$_3$)O), (CF$_2$CF$_2$CF$_2$O), (CF$_2$CF(OX)O), (CF(OX)O), wherein X is as above. They are obtained by photooxidation processes of fluorinated unsaturated monomers as olefins, for example hexafluoropropene, tetrafluoroethylene, perfluoro-vinylethers or mixtures thereof, or by anionic oligomerization of the above unsaturated monomer epoxides.

With catalytic amounts of perfluoropolyoxyalkylenes salts having one or two end groups selected from —OCF$_2$COOZ, —OCF$_2$—CF$_2$ COOZ and —OCF(CF$_3$)COOZ, wherein Z is a monovalent cation selected in the groups Ia and Ib of the Periodic System of the Elements having ionic radius $\geq$0.95 Å or Z is —NR$_4^+$ wherein R is hydrogen or a C$_1$–C$_4$ alkyl, it is meant that the ratio between Z and the —COOH equivalents of the perfluoropolyoxyalkylenes to be decarboxylated ranges from 0.01 to 0.08, preferably from 0.01 to 0.05.

The perfluoropolyoxyalkylene salts used in catalytic amounts are prepared by salification of perfluoropolyoxyalkylenes having at least one end group —OCF$_2$COOH, —OCF$_2$CF$_2$COOH, —OCF(CF$_3$)COOH with compounds of Z monovalent cations as previously defined. Examples of said compounds are hydroxides and the salts of said monovalent cations with weak acids, such for example, acetic, boric, carbonic acid.

As monovalent cations of the group Ia and Ib, $Na^+$, $K^+$, $Rb^+$, $Cs^+$, or $Ag^+$, preferably $K^+$, $Cs^+$, can for example be used.

The Z monovalent cation salts obtained from the same perfluoropolyoxyalkylenes subjected to decarboxylation are preferred.

The results of the invention are surprising since the Applicant has found that the decarboxylation of perfluoropolyoxyalkylenes with —$OCF_2COOH$, —$OCF_2CF_2COOH$ and —$OCF(CF_3)COOH$ end groups, carried out in aqueous medium by heating up to temperatures of 200° C., does not take place.

Some Examples follow for illustrative but not limitative purposes of the invention.

EXAMPLES

Example 1

60.5 g of a α-ω perfluoropolyoxyalkandioicus, equal to $9.3 \times 10^{-2}$ moles obtained by hydrolisis of a fraction having fluoroacyl end groups (—$OCF_2COF$), coming from photo-oxidation of tetrafluoroethylene and oxygen, having structure:

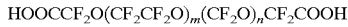

with a m/n ratio=2.4 and a number average molecular weight of 650, are introduced with 200 ml of water into a 400 ml autoclave, suitably coated with a FEP type perfluorinated copolymeric coating, equipped with internal probe for the temperature detection, stirring and manometer for the pressure determination.

6 ml of KOH solution 1M are added so as to salify 3 mmoles of acid, with a ratio in equivalents between salified and free acid end groups equal to 0.033. The pH of the solution is 1.2.

The reactor temperature is brought to 160° C. and maintained for 6 hours. After cooling to room temperature, the reaction mass formed by two phases is discharged. One upper aqueous phase and one lower organic phase which are separated. The organic phase is formed by 49.8 g of fluorinated compound which by the $NMR^{19}F$ and $^1H$ analyses results to have the following structure:

T—$CF_2O(CF_2CF_2O)_m(CF_2O)_nCF_2$—T wherein the T end groups show a 2.9 ratio between the COOH and H end groups. The m/n ratio is 2.4 and the number average molecular weight is 536.

From a balance based on the obtained compound and the end groups it results a conversion of 26% and a selectivity of 99.6%.

Example 2

58.6 g of a α-ω perfluoropolyoxyalkandioic acid, equal to $9 \times 10^{-2}$ moles obtained by hydrolisis of a fraction having fluoroacyl end groups (—$OCF_2COF$), coming from photo-oxidation of tetrafluoroethylene and oxygen, having structure:

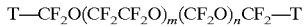

with a m/n ratio=2.4 and a number average molecular weight of 650, are introduced with 160 ml of water into a 500 ml autoclave, suitably coated with a FEP type perfluorinated copolymeric coating, equipped with internal probe for the temperature determination, stirring and manometer for the pressure determination. 5 ml of KOH solution 1M are added so as to salify 2.5 mmoles of acid.

The ratio in equivalents between the salt and the acid is equal to 0.028. The pH of the solution is 1.2.

The reactor temperature is brought to 160° C. and maintained for 10 hours. After cooling to room temperature, the reaction mass formed by two phases is discharged. One upper aqueous phase and one lower organic phase which are separated. The organic phase is formed by 41.4 g of fluorinated compound which by the $NMR^{19}F$ and $^1H$ analyses results to have the following structure:

wherein the T end groups show a 39 ratio between the H and COOH end groups. The m/n ratio is 2.4 and the number average molecular weight is 570.

From a balance based on the obtained compound and on the end groups it results a conversion of 98% and a selectivity of 80.2%.

The so obtained compound is treated with 2 g of $Al_2O_3$ and by filtration 39 g of compound are obtained, having the structure:

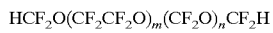

and a number average molecular weight equal to 562 with a m/n ratio=2.4.

Example 3

105 g of a α-ω perfluoropolyoxyalkandioic acid, equal to 110.5 mmoles, obtained by hydrolisis of a fraction having fluoroacyl end groups (—$OCF_2COF$), coming from photo-oxidation of tetrafluoroethylene and oxygen, having structure:

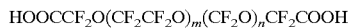

with a m/n ratio=2.6 and a number average molecular weight of 950, are introduced with 250 ml of water into a 500 ml autoclave, suitably coated with a FEP type perfluorinated copolymeric coating, equipped with internal probe for the temperature determination, stirring and manometer for the pressure determination. 22 ml of Cesium Acetate 0.5 M are added so as to salify 11 meq. of acid.

The ratio in equivalents between the salt and the free acid is equal to 0.05. The pH of the solution is 1.4.

The reactor temperature is brought to 130° C. and maintained for 10 hours. After cooling to room temperature, the reaction mass formed by two phases is discharged. One upper aqueous phase and one lower organic phase which are separated. The organic phase is formed by 97 g of fluorinated compound which by the $NMR^{19}F$ and $^1H$ analyses results to have the following structure:

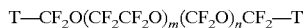

wherein the T end groups show a H/COOH ratio equal to 59. The m/n ratio is 2.6 and the number average molecular weight is 940.

From a balance based on the obtained compound and the end groups it results a conversion of 98.5% and a selectivity of 93.4%.

The so obtained compound is treated with 3 g of $Al_2O_3$ and by filtration 89 g of compound are obtained, having the structure:

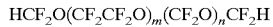

and a number average molecular weight of 935 and a m/n ratio of 2.6.

Example 4 (Comparative)

Example 1 is repeated except that the KOH solution is not added and one works at a temperature of 200° C.

After cooling to room temperature, no pressure variation with respect to the initial conditions is noted. The discharged compound appears biphasic; the heavier phase is separated, dried under vacuum and analyzed by IR and NMR$^{19}$F.

The recovered compound has structure and number average molecular weight equal to those at starting. This shows that the perfluoroalkandioic acids are not decarboxylated in aqueous medium at temperatures up to 200° C.

What is claimed is:

1. A process for preparing perfluoropolyoxyalkylenes having one or two end groups selected from —OCF$_2$H, —OCF$_2$CF$_2$H and —OCF(CF$_3$)H and a number average molecular weight from 120 to 3,000, comprising the decarboxylation of the corresponding perfluoropolyoxyalkylenes having one or two end groups selected from the group consisting of —OCF$_2$COOH, —OCF$_2$CF$_2$COOH, and —OCF(CF$_3$)COOH, in the presence of catalytic amounts of salts formed by perfluoropolyoxyalkylenes having one or two end groups selected from the group consisting of —OCF$_2$COOZ, —OCF$_2$CF$_2$COOZ and —OCF(CF$_3$)COOZ, wherein Z is a monovalent cation selected from the groups Ia and Ib of the Periodic System of the Elements, having ionic radius $\geq 0.95$ Å or Z is —NR$_4^+$ wherein R is hydrogen or a C$_1$–C$_4$ alkyl, wherein ratios between Z and the —COOH equivalents of the perfluoropolyoxyalkylenes to be decarboxylated ranges from 0.01 to 0.08, at a temperature between 120° C. and 180° C., in the presence of water, at pH <5 and at a pressure comprised between 2 and 80 atmospheres.

2. The process according to claim 1, wherein the perfluoropolyoxyalkylenes having at least one end group —OCF$_2$COOH, —OCF$_2$CF$_2$COOH and —OCF(CF$_3$)COOH are formed by perfluorooxyalkylene repeating units, said units being statistically distributed along a polymeric chain, selected from the group consisting of (CF$_2$CF$_2$O), (CF$_2$O), (CF$_2$CF(CF$_3$)O), (CF(CF$_3$)CF$_2$O), (CF(CF$_3$)O), (CF$_2$CF$_2$CF$_2$O), (CF$_2$CF(OX)O), and (CF(OX)O), wherein X is —(R'O)$_u$R" with R'=—CF$_2$—, —CF$_2$CF$_2$—, or —CF$_2$CF(CF$_3$)— and u is an integer from 0 to 6 and where R" is —(CF$_2$)$_k$CF$_3$ and k is an integer from 0 to 4.

3. The process according to claim 1, wherein the perfluoropolyoxyalkylenes having at least one end group —OCF$_2$COOH, —OCF$_2$CF$_2$—COOH and —OCF(CF$_3$)COOH have the following structures:

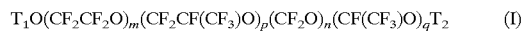

or

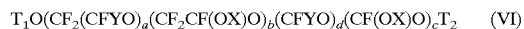

wherein T$_2$ is selected from —CF$_2$COOH, —CF$_2$CF$_2$COOH, or —CF(CF$_3$)COOH; T$_1$ is selected from —CF$_3$, —C$_2$F$_5$, —C$_3$F$_7$, —CF$_2$COOH, —CF$_2$CF$_2$COOH, or —CF(CF$_3$)COOH; Y=—F, or —CF$_3$, and X is —(R'O)$_u$R" with R'=—CF$_2$—, —CF$_2$CF$_2$—, or —CF$_2$CF(CF$_3$)— and u is an integer from 0 to 6 and where R" is —(CF$_2$)$_k$CF$_3$ and k is an integer from 0 to 4; r is 0 or 1 and a, b, c, d, m, n, p, q, and s have average values such that the number average molecular weight is comprised between 120 and 3,000.

4. The process according to claim 1, wherein the monovalent cations Z are selected from Na$^+$, K$^+$, Rb$^+$, Cs$^+$, or Ag$^+$.

5. The process according to claim 1, wherein the Z monovalent cation salts are obtained from the same perfluoropolyoxyalkylenes subjected to decarboxylation.

6. The process according to claim 1, wherein the ratios between Z and the —COOH equivalent of the perfluoropolyoxyalkylenes to be decarboxylated ranges from 0.01 to 0.05.

7. The process according to claim 1, wherein said pressure is between 3 and 40 atmospheres.

8. The process according to claim 4, wherein the monovalent cations Z are selected from K$^+$ or Cs$^+$.

* * * * *